United States Patent

Fujii et al.

Patent Number: 5,552,557
Date of Patent: Sep. 3, 1996

[54] PROCESS FOR PREPARING 2-CYANOIMIDAZOLE COMPOUNDS BY REACTION OF AN AMINO KETONE COMPOUND

[75] Inventors: Yasuhiro Fujii; Toyoshi Tanimura, both of Shiga, Japan

[73] Assignee: Ishihara Sangyo Kaisha, Ltd., Osaka, Japan

[21] Appl. No.: 337,523

[22] Filed: Nov. 9, 1994

[30] Foreign Application Priority Data

Nov. 12, 1993 [JP] Japan ................................. 5-307346
Mar. 25, 1994 [JP] Japan ................................. 6-079703

[51] Int. Cl.$^6$ ................. C07D 233/90; C07D 233/68
[52] U.S. Cl. ........................................................ 548/337.1
[58] Field of Search ............................................ 548/337.1

[56] References Cited

U.S. PATENT DOCUMENTS 3,806,517  4/1974  Begland ............................... 548/337.1
4,995,898  2/1991  Nasu et al. ........................ 548/337.1 X

FOREIGN PATENT DOCUMENTS 3099065  4/1991  Japan ................................. 548/337.1

*Primary Examiner*—Floyd D. Higel
*Attorney, Agent, or Firm*—Sughrue, Mion, Zinn, Macpeak & Seas

[57] ABSTRACT

A process for preparing 2-cyanoimidazole compounds represented by the following formula (I):

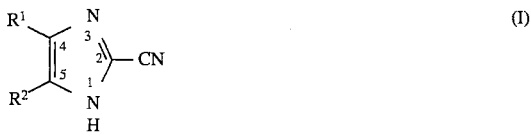

wherein $R^1$ and $R^2$ each independently represents a hydrogen atom, an alkyl group which may be substituted, a phenyl group which may be substituted or a heterocyclic group which may be substituted and $R^1$ and $R^2$ may join together to form an alkylene group which may be substituted, which comprises undergoing reaction of a compound represented by the following formula (II):

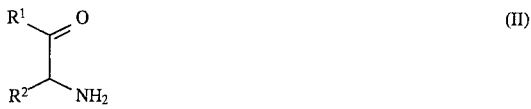

wherein $R^1$ and $R^2$ are as defined above or salt thereof with cyanogen.

10 Claims, No Drawings

PROCESS FOR PREPARING 2-CYANOIMIDAZOLE COMPOUNDS BY REACTION OF AN AMINO KETONE COMPOUND

FIELD OF THE INVENTION

The present invention relates to a novel process for preparing 2-cyanoimidazole compounds. 2-Cyanoimidazole compounds are useful as intermediates of agricultural chemicals or medicines.

BACKGROUND OF THE INVENTION

As for the method of obtaining 2-cyanoimidazole compounds, there have heretofore been known methods which comprise introducing a cyano group to the corresponding imidazole derivatives at the 2-position (cf., U.S. Pat. No. 4,995,898).

In such known methods, it is necessary to perform a multi step sequence to obtain 2-cyanoimidazole compounds. In such cases, independent procedure is required for the formation of imidazole ring and the cyanation of the imidazole ring. Moreover, the cyanation procedures often require complicated processes. These known methods are not advantageous for the commercial production of 2-cyanoimidazole compounds.

SUMMARY OF THE INVENTION

It is an object of the present invention to provide a novel and advantageous process for commercially preparing 2-cyanoimidazole compounds.

The foregoing object of the present invention will become more apparent from the following detailed description and examples.

The inventors made extensive studies of processes for preparing 2-cyanoimidazole compounds. As a result, a new reaction has been found by which 2-cyanoimidazole compounds can be easily obtained by single step and raw materials in the reaction are readily available. Thus, the present invention has been worked out.

The present invention relates to a process for preparing 2-cyanoimidazole compounds represented by the following formula (I):

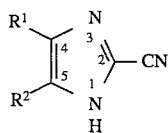

(I)

wherein $R^1$ and $R^2$ each independently represents a hydrogen atom, an alkyl group which may be substituted, a phenyl group which may be substituted or a heterocyclic group which may be substituted and $R^1$ and $R^2$ may join together to form an alkylene group which may be substituted, which comprises undergoing reaction of a compound represented by the following formula (II):

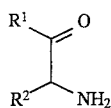

(II)

wherein $R^1$ and $R^2$ are as defined above or salt thereof with cyanogen.

DETAILED DESCRIPTION OF THE INVENTION

As the substituents on the alkyl group represented by $R^1$ or $R^2$ which may be substituted there may be selected from those which have no adverse effects on the reaction, i.e., a halogen atom, a haloalkyl group, an alkoxy group, a haloalkoxy group, an alkylthio group, a haloalkylthio group, an aryl group, an aryloxy group, an arylthio group, a heteroaryl group, a heteroaryloxy group, a heteroarylthio group, an alkylamino group, a dialkylamino group. One or more of these substituents may be on the alkyl group. If there are two or more substituents, they may be the same or different.

Examples of the alkyl group represented by $R^1$ or $R^2$ which may be substituted generally include $C_{1-10}$ straight-chain or branched alkyl groups. Specific examples of such alkyl groups include a methyl group, an ethyl group, an n-propyl group, an n-butyl group, an n-pentyl group, an n-hexyl group, an isopropyl group, a sec-butyl group, an isobutyl group, a cyclopropyl group, a cyclobutyl group, a cyclopentyl group, and a cyclohexyl group.

As the substituents on the phenyl, heterocyclic or alkylene group represented by $R^1$ or $R^2$ which may be substituted there may be selected from those which have no adverse effects on the reaction, i.e., a halogen atom, an alkyl group, a haloalkyl group, an alkoxy group, a haloalkoxy group, an alkylthio group, a haloalkylthio group, an aryl group, an aryloxy group, an arylthio group, a heteroaryl group, a heteroaryloxy group, a heteroarylthio group, an alkylamino group, a dialkylamino group. One or more of these substituents may be on the phenyl, heterocyclic or alkylene group. If there are two or more substituents, they may be the same or different.

Examples of the heterocyclic group represented by $R^1$ or $R^2$ which may be substituted include 3- to 10-membered heterocyclic groups containing 1 to 4 hetero atoms selected from the group consisting of a nitrogen atom, an oxygen atom and a sulfur atom and a balance of carbon atoms. Specific examples of such heterocyclic groups include a pyridyl group, a pyrimidinyl group, a pyridazinyl group, a triazinyl group, a furyl group, a thienyl group, a pyrrolidyl group, an imidazolyl group, an oxazolyl group, and a thiazolyl group.

Examples of the alkylene group represented by $R^1$ or $R^2$ which may be substituted generally include $C_{2-8}$ straight-chain alkylene groups. Specific examples of such alkylene groups include 1,3-propanediyl, 1,4-butanediyl, and 1,5-pentanediyl.

Examples of halogen atoms as the substituents on the alkyl, phenyl, heterocyclic or alkylene group represented by $R^1$ or $R^2$ which may be substituted include a fluorine atom, a chlorine atom, a bromine atom, and an iodine atom. Examples of various moieties in the substituents on the alkyl, phenyl, heterocyclic or alkylene group represented by $R^1$ or $R^2$ which may be substituted are as follows. Examples of the alkyl moiety include a methyl group, an ethyl group, and a propyl group. Examples of the aryl moiety include a phenyl group, and a naphthyl group. Examples of the heteroaryl moiety include a pyridyl group, a pyrimidinyl group, a pyridazinyl group, a triazinyl group, a furyl group, a thienyl group, a pyrolidyl group, an imidazolyl group, an oxazolyl group, and a thiazolyl group.

Examples of the salt of the compound represented by the formula (II) include a hydrochloride, a hydrobromide, a sulfate, a nitrate, and a methanesulfonate.

The method of the present invention may be preferably applied to the preparation of the following compounds:

(1) Compound wherein $R^1$ is an alkyl, phenyl or heterocyclic group which may be substituted and $R^2$ is a hydrogen atom in the formula (I) and (2) Compound wherein $R^1$ is a phenyl group which may be substituted and $R^2$ is a hydrogen atom in the formula (I)

Specific examples of the compound of the formula (II) to be used as a starting material in the present invention include aminoacetone, ethyl aminomethyl ketone, 2-chloroethyl aminomethyl ketone, 3,3,3-trifluoropropyl aminomethyl ketone, 2-methoxyethyl aminomethyl ketone, aminomethyl benzyl ketone, aminomethyl 4-chlorobenzyl ketone, 2-amino-2'-methylacetophenone, 2-amino-2'-ethylacetophenone, 2-amino-3'-ethylacetophenone, 2-amino-4'-ethylacetophenone, 2-amino- 2',3'-dimethylacetophenone, 2-amino-2',4'-dimethylacetophenone, 2-amino-2'-chloroacetophenone, 2-amino-3'-chloroacetophenone, 2-amino-4'-chloroacetophenone, 2-amino- 2',4'-dichloroacetophenone, 2-amino-2'-bromoacetophenone, 2-amino-3'-bromoacetophenone, 2-amino-2'-trifluoromethylacetophenone, 2-amino-3'-trifluoromethylacetophenone, 2-amino-4'-trifluoromethylacetophenone, 2-amino-4-phenylacetophenone, 4-pyridyl aminomethyl ketone, 5-trifluoromethyl-2-pyridyl aminomethyl ketone, 2-pyrimidinyl aminomethyl ketone, 2-aminocyclohexanone, 1-aminoethyl methyl ketone, 1-aminoethyl propyl ketone, 2-aminopropionophenone, 2-amino-4'-methylpropionophenone, and 4-pyridyl 1-aminoethyl ketone.

In the method of the present invention, the compound represented by the formula (II) is preferably used in the form of salt with an appropriate acid.

The amount of cyanogen to be used is preferably in the range of not less than 1 equivalent based on the amount of the compound represented by the formula (II).

In the method of the present invention, a base may be used. As such a base there may be used either an inorganic base or an organic base. Examples of the inorganic base include a hydroxide of an alkali metal such as sodium hydroxide and potassium hydroxide, a carbonate of an alkali metal or an alkaline earth metal such as potassium carbonate, calcium carbonate and sodium hydrogencarbonate, an acetate of an alkali metal such as sodium acetate and potassium acetate, a hydride of an alkali metal such as sodium hydride, a metallic alkoxide such as sodium methoxide, and an alkali metal such as metallic sodium. Examples of the organic base include triethylamine, pyridine, picoline, and N,N-dimethyl-aniline. The amount of the base to be used may range from the catalytic amount to large excess.

In the present invention, a solvent may be used. Examples of such a solvent include aromatic hydrocarbons such as benzene, toluene, xylene and chlorobenzene, cyclic or acyclic aliphatic hydrocarbons such as chloroform, carbon tetrachloride, methylene chloride, dichloroethane, trichloroethane, n-hexane and cyclohexane, ethers such as diethyl ether, dioxane, tetrahydrofuran and dimethoxyethane, ketones such as acetone, methyl ethyl ketone and methyl isobutyl ketone, nitriles such as acetonitrile and propionitrile, aprotic polar solvents such as N,N-dimethylformamide, N-methylpyrrolidone, dimethyl sulfoxide and Sulfolane (i.e., tetrahydrothiophene 1,1-dioxide), alcohols such as methanol and ethanol, and pyridine.

The reaction temperature is normally in the range of from 0° to 120° C., preferably from 40° to 110° C., where the reaction is completed in several hours to scores of hours.

After the completion of the reaction, the reaction product can be subjected to ordinary work up procedures such as extraction and recrystallization to obtain a 2-cyanoimidazole compound represented by the formula (I).

Preferred embodiments of the method of the present invention will be described below, but the present invention should not be construed as being limited thereto.

(1) Cyanogen is reacted with the compound represented by the formula (II) or salt thereof in an amount of 1 to 10 mol based on 1 mol of the latter at a temperature of from 40° to 110° C.

(2) The reaction is effected in the presence of a solvent in an amount of 0.01 to 10 l based on 1 mol of cyanogen.

(3) Cyanogen and the solvent are premixed before use.

(4) As the solvent there is used one or a mixture of two or more selected from the group consisting of aromatic hydrocarbons such as benzene, toluene, and xylene, cyclic or acyclic aliphatic hydrocarbons such as chloroform, methylene chloride, and 1,2-dichloroethane, ethers such as 1,4-dioxane, and 1,2-dimethoxyethane, ketones such as acetone, nitriles such as acetonitrile and propionitrile, and aprotic polar solvents such as N,N-dimethylformamide, and dimethyl sulfoxide.

(5) The reaction is effected in the presence of a base in an amount of the catalytic amount (e.g., 0.001 mol) to 5 mol based on 1 mol of the compound represented by the formula (II) or salt thereof.

(6) As the base there is used pyridine or N,N-dimethylaniline.

The present invention will be further described in the following examples, but the present invention should not be construed as being limited thereto.

EXAMPLE 1

Preparation of 2-cyano-4-phenylimidazole 0.85 g (5 mmol) of 2-aminoacetophenone hydrochloride and 1.98 g (25 mmol) of pyridine were dissolved in 30 ml of N,N-dimethylformamide in a four-necked flask equipped with a dry ice condenser. The solution was then cooled to a temperature of −50° C. To the solution was then added about 0.5 g (9.6 mmol) of cyanogen which had been cooled and solidified at a temperature of −50° C. The solution was heated at a temperature of 60° C. for 1 hour, and at a temperature of 80° C. for 1 hour. The reaction solution was then extracted with ethyl acetate and water. The resulting organic phase was then washed with saturated brine. The organic phase was dried over anhydrous sodium sulfate, and then concentrated. The material was then subjected to silica gel column chromatography to obtain 0.29 g (yield: 34 %) of 2-cyano-4-phenylimidazole.

EXAMPLE 2

Preparation of 2-cyano-4-(p-tolyl)imidazole 0.93 g (5 mmol) of 2-amino-4'-methylacetophenone hydrochloride was suspended in 30 ml of toluene in a 50-ml stainless steel autoclave. To the suspension was then added 0.79 g (10 mmol) of pyridine. The suspension was then cooled to a temperature of −78° C. To the suspension was then added about 0.5 g (9.6 mmol) of cyanogen which had been cooled and solidified at a temperature of −78° C. The autoclave was then sealed. The suspension was heated at a temperature of 100° C. for 2.5 hours, and then allowed to cool. The content was then taken out of the autoclave. The reaction mixture was then extracted with ethyl acetate and water. The resulting organic phase was dried over anhydrous sodium sulfate, and then subjected to silica gel column chromatography to obtain 0.48 g (yield: 52 %) of 2-cyano-4-(p-tolyl)imidazole.

EXAMPLE 3

Preparation of 2-cyano-4-(p-tolyl)imidazole 2.0 g (11 mmol) of 2-amino-4'-methylacetophenone hydrochloride was measured out in a 100-ml round bottom flask. To the material was then added 40 ml (40 mmol) of a 1 mol/l N,N-dimethylformamide solution of cyanogen at a temperature of 0° C. To the mixture was then added 1.7 g (22 mmol) of pyridine. The mixture was then heated at a temperature of 60° C. with stirring for 18 hours. The reaction mixture was then allowed to cool to room temperature. The reaction mixture was extracted with ethyl acetate and water. The resulting organic phase was washed with saturated brine. The organic phase was dried over anhydrous sodium sulfate, concentrated, and then subjected to silica gel column chromatography to obtain 1.55 g (yield: 77 %) of 2-cyano-4-(p-tolyl)imidazole.

EXAMPLE 4

Preparation of 2-cyano-4-(p-tolyl)imidazole 15 g (81 mmol) of 2-amino-4'-methylacetophenone hydrochloride was measured out in a 200-ml four-necked flask. To the material was then added 121 ml (121 mmol) of a 1 mol/l N,N-dimethylformamide solution of cyanogen. The mixture was then stirred. To the mixture was then added 29.4 g (243 mmol) of N,N-dimethylaniline. The mixture was then heated at a temperature of 100° C. with stirring for 3 hours. N,N-dimethylaniline was then distilled off from the reaction mixture under a pressure of 30 mmHg. The reaction mixture was then allowed to cool to room temperature. 200 ml of water was then poured into the reaction mixture. The reaction mixture was acidified with hydrochloric acid, and a precipitate was recovered by filtration. The filtration residue was dissolved in 200 ml of a 5% aqueous solution of sodium hydroxide, and the solution was filtered. The filtrate was then acidified with hydrochloric acid. 2-Cyano-4-(p-tolyl)imidazole as a desired compound was then recovered by filtration. The material was then dried to obtain 12.43 g of a desired compound with a purity of 83.4% (yield: 70.0%).

The foregoing preparation methods or examples also allow the syntheses of the following 2-cyanoimidazole compounds:

2-Cyano-4-(o-tolyl)imidazole;
2-Cyano-4-(m-tolyl)imidazole;
2-Cyano-4-(2-ethylphenyl)imidazole;
2-Cyano-4-(3-ethylphenyl)imidazole;
2-Cyano-4-(4-ethylphenyl)imidazole;
2-Cyano-4-(2,3-dimethylphenyl)imidazole;
2-Cyano-4-(2,4-dimethylphenyl)imidazole;
4-(2-Chlorophenyl)-2-cyanoimidazole;
4-(3-Chlorophenyl)-2cyanoimidazole;
4-(4-Chlorophenyl)-2-cyanoimidazole;
2-Cyano-4-(2,4-dichlorophenyl)imidazole;
4-(2-Bromophenyl)-2-cyanoimidazole;
4-(3-Bromophenyl)-2-cyanoimidazole;
4-(4-Bromophenyl)-2-cyanoimidazole;
2-Cyano-4-(2-trifluoromethylphenyl)imidazole;
2-Cyano-4-(3-trifluoromethylphenyl)imidazole;
2-Cyano-4-(4-trifluoromethylphenyl)imidazole;
2-Cyano-4-(4-phenylphenyl)imidazole;
2-Cyano-4-methylimidazole;
2-Cyano-4-ethylimidazole;
4-(2-Chloroethyl)-2-cyanoimidazole;
2-Cyano-4-(3,3,3-trifluoropropyl)imidazole;
2-Cyano-4-(2-methoxyethyl)imidazole;
2-Cyano-5-methyl-4-phenylimidazole;
2-Cyano-5-methyl-4-(p-tolyl)imidazole;
2-Cyano-4,5-dimethylimidazole;
2-Cyano-4-n-propyl-5-methylimidazole;
4-Benzyl-2-cyanoimidazole;
4-(m-Chlorobenzyl)-2-cyanoimidazole;
2-Cyano-4-(4-pyridyl)imidazole;
2-Cyano-4-(5-trifluoromethyl-2-pyridyl)imidazole;
2-Cyano-5-methyl-4-(4-pyridyl)imidazole;
2-Cyano-4-(2-pyrimidinyl)imidazole;
2-Cyano-4,5,6,7-tetrahydrobenzimidazole As mentioned above, the present invention provides a novel process for preparing 2-cyanoimidazole compounds. By the result of the present invention, 2-cyanoimidazole compounds can be easily obtained in one step.

While the invention has been described in detail and with reference to specific embodiments thereof, it will be apparent to one skilled in the art that various changes and modifications can be made therein without departing from the spirit and scope thereof.

What is claimed is:
1. A process for preparing a 2-cyanoimidazole compound represented by the following formula (I):

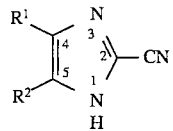

wherein $R^1$ and $R^2$ each independently represents hydrogen, an unsubstituted alkyl group or an alkyl group substituted with at least one substituent selected from the group consisting of halogen, haloalkyl, alkoxy, haloalkoxy, alkylthio, haloalkylthio, aryl, aryloxy, arylthio, heteroaryl, heteroaryloxy, heteroarylthio, alkylamino, and dialkylamino, an unsubstituted phenyl group or a phenyl group substituted with at least one substituent selected from the group consisting of halogen, alkyl, haloalkyl, alkoxy, haloalkoxy, alkylthio, haloalkylthio, aryl, aryloxy, arylthio, heteroaryl, heteroaryloxy, heteroarylthio, alkylamino, and dialkylamino, or a 3-to-10-membered heterocyclic group which contains 1 to 4 hetero atoms selected from the group consisting of nitrogen, oxygen and sulfur and a balance of carbon atoms, and said heterocyclic group is unsubstituted or is substituted with at least one substituent selected from the group consisting of halogen, alkyl, haloalkyl, alkoxy, haloalkoxy, alkylthio, haloalkylthio, aryl, aryloxy, arylthio, heteroaryl, heteroaryloxy, heteroarylthio, alkylamino, and dialkylamino, or $R^1$ and $R^2$ when joined together form an alkylene group which may be substituted with at least one substituent selected from the group consisting of halogen, alkyl, haloalkyl, alkoxy, haloalkoxy, alkylthio, haloalkylthio, aryl, aryloxy, arylthio, heteroaryl, heteroaryloxy, heteroarylthio, alkylamino, and dialkylamino, which process comprises reacting cyanogen with a compound represented by the following formula (II):

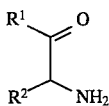 (II)

wherein $R^1$ and $R^2$ are as defined above or a salt thereof.

2. The process according to claim 1, wherein $R^2$ is a hydrogen atom.

3. The process according to claim 1, wherein $R^1$ is an unsubstituted or a substituted phenyl group and $R^2$ is a hydrogen atom.

4. The process according to claim 1, wherein cyanogen is reacted with the compound represented by the formula (II) or salt thereof in an amount of 1 to 10 mols based on 1 mol of the latter at a temperature of from 0° to 120° C.

5. The process according to claim 4, wherein the reaction temperature is in the range of from 40° to 110° C.

6. The process according to claim 4, wherein the reaction is effected in the presence of a solvent in an amount of 0.01 to 10 l based on 1 mol of cyanogen.

7. The process according to claim 6, wherein cyanogen and the solvent are premixed prior to the reaction.

8. The process according to claim 6, wherein said solvent is one or a mixture of two or more selected from the group consisting of aromatic hydrocarbons, cyclic or acyclic aliphatic hydrocarbons, ethers, ketones, nitriles and aprotic polar solvents.

9. The process according to claim 4, wherein the reaction is effected in the presence of a base in an amount of from the catalytic amount to 5 mol based on 1 mol of the compound represented by the formula (II) or salt thereof.

10. The process according to claim 9, wherein said base is pyridine or N,N-dimethylaniline.

* * * * *